US00PP22585P2

(12) United States Plant Patent

Gomez Bullis

(10) Patent No.: US PP22,585 P2

(45) Date of Patent: Mar. 13, 2012

(54) *NEOREGELIA* PLANT NAMED 'PURPLE PASSION'

(50) Latin Name: ***Neoregelia 'Takamura Princeps'×Neoregelia* hybrid**
Varietal Denomination: Purple Passion

(75) Inventor: Patricia E. Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 14 days.

(21) Appl. No.: 12/806,828

(22) Filed: Aug. 21, 2010

(51) Int. Cl.
*A01H 5/00* (2006.01)

(52) U.S. Cl. ..... Plt./370

(58) Field of Classification Search ..... Plt./370
See application file for complete search history.

*Primary Examiner* — June Hwu

(74) *Attorney, Agent, or Firm* — C. A. Whealy

(57) ABSTRACT

A new and distinct cultivar of *Neoregelia* plant named 'Purple Passion', characterized by its upright and outwardly arching growth habit; broad glossy green and purple-colored lower leaves; broad glossy red purple-colored upper leaves; good interiorscape and landscape performance; and resistance to *Exserohilium.*

1 Drawing Sheet

Botanical designation: *Neoregelia 'Takamura Princeps'*× *Neoregelia* hybrid.

Cultivar denomination: 'PURPLE PASSION'.

BACKGROUND OF THE INVENTION

The present invention relates to a new and distinct cultivar of *Neoregelia* plant, botanically known as *Neoregelia 'Takamura Princeps'*×*Neoregelia* hybrid, and hereinafter referred to by the name 'Purple Passion'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of an unnamed proprietary selection of *Neoregelia 'Takamura Princeps'*, not patented, as the female, or seed, parent with *Neoregelia* hybrid 'Purple Star', not patented, as the male, or pollen, parent. The new *Neoregelia* plant was discovered and selected by the Inventor as a single plant within the progeny of the stated cross-pollination in a controlled greenhouse environment in Princeton, Fla. in 2002.

Asexual reproduction of the new *Neoregelia* plant by offsets in a controlled environment in Princeton, Fla. since 2003, has shown that the unique features of this new *Neoregelia* plant are stable and reproduced true to type in successive generations.

SUMMARY OF THE INVENTION

Plants of the new *Neoregelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Purple Passion'. These characteristics in combination distinguish 'Purple Passion' as a new and distinct cultivar of *Neoregelia*:

1. Upright and outwardly arching growth habit.
2. Broad glossy green and purple-colored lower leaves.
3. Broad glossy red purple-colored upper leaves.
4. Good interiorscape and landscape performance.
5. Resistant to *Exserohilium.*

Plants of the new *Neoregelia* differ primarily from plants of the female parent selection in the following characteristics:

1. Plants of the new *Neoregelia* have broader leaves than plants of the female parent selection.
2. Plants of the new *Neoregelia* do not require flower bud initiation to develop leaf coloration whereas plants of the female parent selection require flower bud initiation to develop leaf coloration.
3. Plants of the new *Neoregelia* and the female parent selection differ in leaf coloration.
4. Plants of the new *Neoregelia* are more cold temperature tolerant than plants of the female parent selection.

Plants of the new *Neoregelia* differ primarily from plants of the male parent, 'Purple Star', in the following characteristics:

1. Plants of the new *Neoregelia* are denser, not as broad and have shorter leaves than plants of 'Purple Star'.
2. Leaves of plants of the new *Neoregelia* are glossier than leaves of plants of 'Purple Star'.
3. Plants of the new *Neoregelia* do not require flower bud initiation to develop leaf coloration whereas plants of 'Purple Star' require flower bud initiation to develop leaf coloration.
4. Plants of the new *Neoregelia* are more resistant to *Exserohilium* than plants of 'Purple Star'.

Plants of the new *Neoregelia* can be compared to plants of the *Neoregelia* 'Royal Burgundy', not patented. In side-by-side comparisons conducted in Princeton, Fla., plants of the new *Neoregelia* and 'Royal Burgundy' differed primarily in the following characteristics:

1. Plants of the new *Neoregelia* had broader leaves than plants of 'Royal Burgundy'.
2. Leaves of plants of the new *Neoregelia* were glossier than leaves of plants of 'Royal Burgundy'.

3. Plants of the new *Neoregelia* did not require flower bud initiation to develop leaf coloration whereas plants of 'Royal Burgundy' required flower bud initiation to develop leaf coloration.
4. Plants of the new *Neoregelia* were more tolerant to low light conditions than plants of 'Royal Burgundy'.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph at the bottom of the sheet is a side perspective view of a typical flowering plant of 'Purple Passion' grown in a container.

The photograph at the top of the sheet is a top perspective view of a typical flowering plant of 'Purple Passion'.

DETAILED BOTANICAL DESCRIPTION

The aforementioned photographs and following observations, measurements and values describe flowering plants grown during the spring in 15-cm containers in a polypropylene-covered greenhouse in Princeton, Fla. under commercial *Neoregelia* production practices. During the production of the plants, day temperatures ranged from 10° C. to 32° C., night temperatures ranged from 7° C. to 32° C. and light levels averaged 3,200 foot-candles. Plants were one year old when the photographs and description were taken. In the following description, color references are made to The Royal Horticultural Society Colour Chart, 2007 Edition, except where general terms of ordinary dictionary significance are used.

Botanical classification: *Neoregelia 'Takamura Princeps'*× *Neoregelia* hybrid 'Purple Passion'.

Parentage:

*Female, or seed, parent.*—Unnamed proprietary selection of *Neoregelia 'Takamura Princeps'*, not patented.

*Male, or pollen, parent.*—*Neoregelia* hybrid 'Purple Star', not patented.

Propagation:

*Type.*—By offsets.

*Time to initiate roots, summer.*—About 30 days at 30° C. to 32° C.

*Time to initiate roots, winter.*—About 45 days at 30° C. to 32° C.

*Time to produce a rooted young plant, summer.*—About three to four months at 30° C. to 32° C.

*Time to produce a rooted young plant, winter.*—About four to five months at 18° C. to 22° C.

*Root description.*—Medium in thickness, fibrous; yellow to tan in color.

*Rooting habit.*—Moderately freely branching; medium density.

Plant description:

*Plant form/growth habit.*—Upright and outwardly arching growth habit; rosette leaves are erect when young, becoming outwardly arching with development; plants readily produce uniform offsets; vigorous growth habit.

*Plant height.*—About 18 cm.

*Plant diameter or spread.*—About 37 cm.

*Internode length.*—About 4 mm.

*Stem texture.*—Smooth, glabrous.

*Stem color.*—Close to NN155B.

Foliage description:

*Arrangement.*—Rosette, spiral phyllotaxis; simple; sessile, clasping.

*Shape.*—Oblong.

*Apex.*—Cuspidate.

*Base.*—Truncate.

*Margin.*—Senate; spinose.

*Length.*—About 25 cm.

*Width, mid-section.*—About 7 cm.

*Width, base.*—About 9.2 cm.

*Texture.*—Smooth, glabrous; leathery.

*Luster.*—Glossy.

*Venation pattern.*—Parallel.

*Color.*—Lower leaves, upper surface: Close to 146A overlain with close to 184B; towards the apex, close to 146A overlain with close to 187A; venation, close to 200B. Lower leaves, lower surface: Towards the apex, close to N199B; towards the base, close to 183B; venation, close to 187B. Upper leaves, upper surface: Close to 71A; towards the base, close to 157D; venation, close to 200B. Upper leaves, lower surface: Close to 71A; venation, close to 187B.

Inflorescence description:

*Inflorescence form.*—Terminal flat-topped compact corymb located inside the leaf rosette; about 138 flowers develop per inflorescence.

*Time to flower.*—Plants begin flowering about ten to twelve weeks after planting; plants flower naturally during the spring in Florida.

*Flower longevity.*—Individual flowers last about two to three days on the plant; flowers persistent.

*Fragrance.*—None detected.

*Inflorescence length.*—About 7.5 cm.

*Inflorescence diameter.*—About 5.5 cm.

*Flower size.*—Length: About 5.9 cm. Diameter: About 7 mm.

*Flower buds.*—Length: About 4.5 cm. Diameter: About 6 mm. Shape: Narrowly elongate. Color: Close to 91C.

*Petals.*—Quantity per flower: Three in a single whorl. Shape: Oblanceolate. Apex: Acuminate. Base: Truncate. Margin: Entire. Length: About 4 cm. Width: About 6 mm. Texture: Smooth, glabrous. Color: When opening, upper surface: Close to 93D. When opening, lower surface: Close to 97C. Fully opened, upper. surface: Close to NN155D; towards the apex, center close to 93D and margins, close to 92C. Fully opened, lower surface: Close to NN155D; towards the apex, close to 92C to 92D.

*Flower bracts.*—Quantity per flower: One. Shape: Oblanceolate. Length: About 4 cm. Width: About 7 mm. Texture: Membraneous. Color: Towards the apex, close to 183B; towards the base, close to 157D.

*Sepals.*—Quantity per flower: Three in a single whorl. Shape: Narrowly elliptic. Apex: Acuminate. Base: Truncate. Margin: Entire. Length: About 2.8 cm. Width: About 8 mm. Texture: Smooth, glabrous. Color, upper surface: Close to 145B. Color, lower surface: Close to 146C; towards the apex, close to 146A; towards the base, close to 145C.

*Peduncles.*—Length: About 1.2 cm. Diameter: About 1.5 cm. Strength: Strong. Aspect: Typically erect. Texture: Smooth, glabrous. Color: Close to NN155B.

*Pedicels.*—Length: About 7 mm. Diameter: About 3 mm. Strength: Strong. Aspect: Typically erect to somewhat outward and curving upright. Texture: Smooth, glabrous. Color: Close to NN155D.

*Stamens.*—Quantity per flower: Six. Filament length: About 2.2 cm; partially adnate to the petals. Filament color: Close to NN155D. Anther shape: Lanceolate. Anther length: About 5 mm. Anther color: Close to 155A. Pollen amount: Scarce. Pollen color: Close to 158C.

*Pistils.*—Quantity per flower: One. Pistil length: About 4.7 cm. Stigma shape: Oval, elongated. Stigma color: Close to N155C. Style length: About 2.6 cm. Style color: Close to NN155D. Ovary color: Close to NN155C.

*Fruit/seed.*—Fruit and seed production have not been observed on plants of the new *Neoregelia*.

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions and to have good garden performance.

Disease/pest resistance: Plants of the new *Neoregelia* have been observed to be resistant to *Exserohilium*. Resistance to pests and other pathogens common to *Neoregelia* plants has not been observed.

It is claimed:

1. A new and distinct *Neoregelia* plant named 'Purple Passion' as illustrated and described.

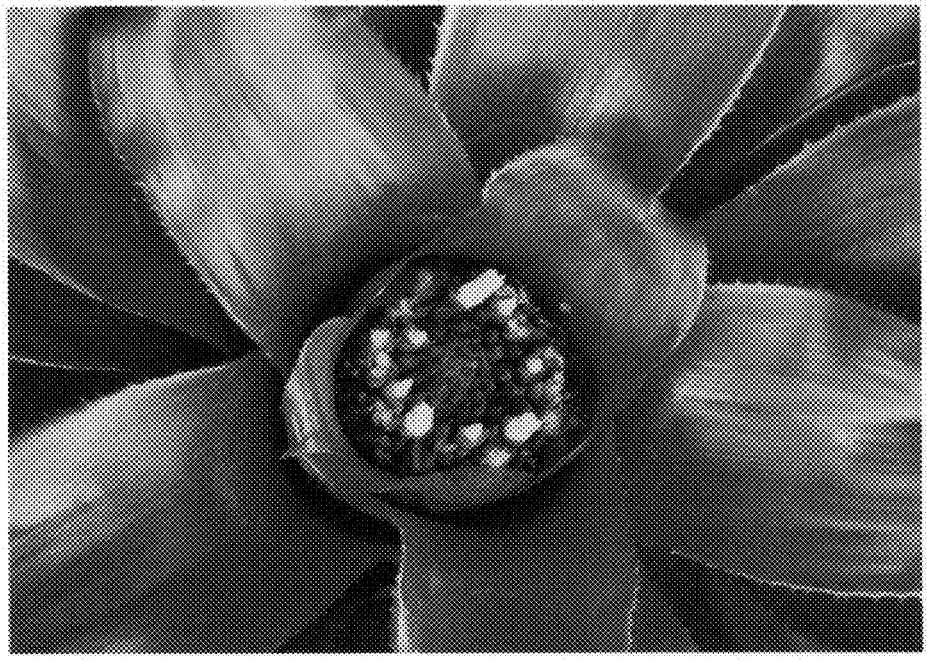
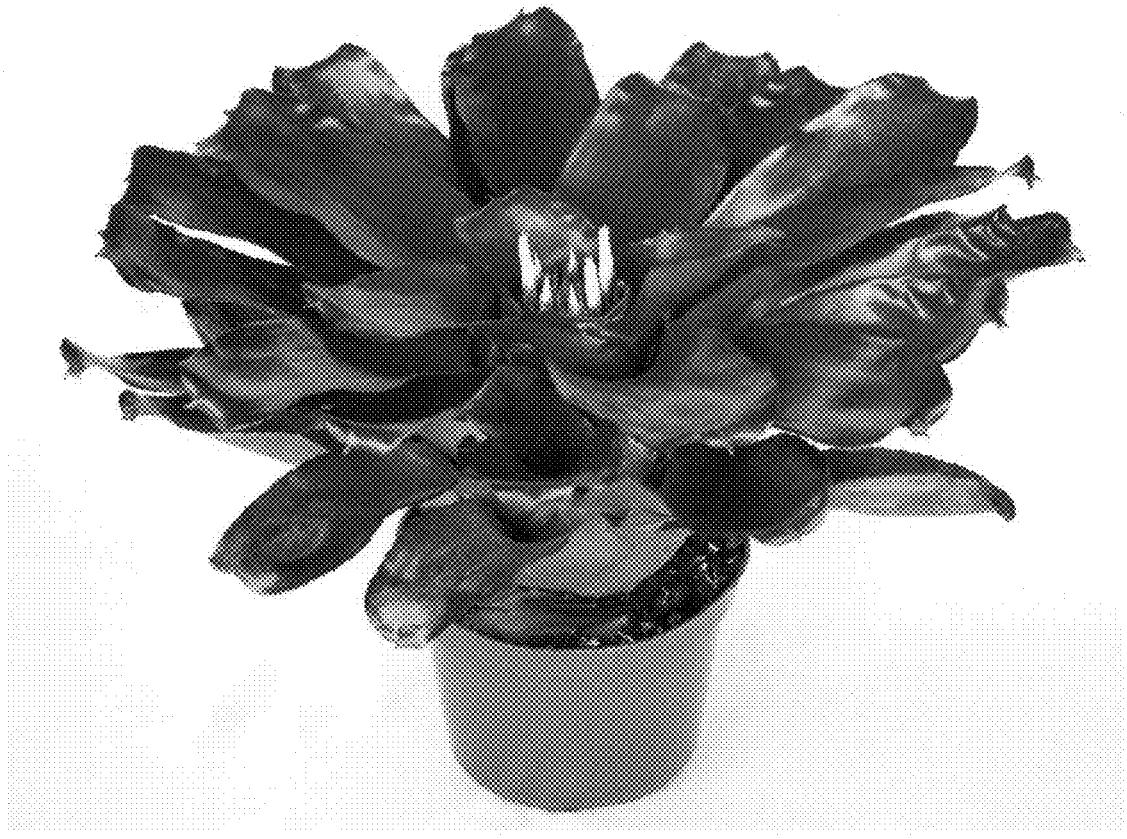

* * * * *